(12) United States Patent
Ma et al.

(10) Patent No.: US 8,562,668 B2
(45) Date of Patent: Oct. 22, 2013

(54) IMPLANT HAVING HIGH FATIGUE RESISTANCE, DELIVERY SYSTEM, AND METHOD OF USE

(75) Inventors: Jianlu Ma, Maple Grove, MN (US); Joe Tatalovich, St. Louis Park, MN (US); Lixiao Wang, Long Lake, MN (US); Xiaoling Zhao, Maple Grove, MN (US); Dan Ranum, Golden Valley, MN (US)

(73) Assignee: Covidien LP, Mansfield, MA (US)

( * ) Notice: Subject to any disclaimer, the term of this patent is extended or adjusted under 35 U.S.C. 154(b) by 522 days.

(21) Appl. No.: 11/764,336

(22) Filed: Jun. 18, 2007

(65) Prior Publication Data
US 2007/0289677 A1 Dec. 20, 2007

Related U.S. Application Data

(60) Provisional application No. 60/840,170, filed on Aug. 25, 2006, provisional application No. 60/814,437, filed on Jun. 16, 2006.

(51) Int. Cl.
*A61F 2/82* (2013.01)
(52) U.S. Cl.
USPC ..................................... 623/1.18; 623/1.19
(58) Field of Classification Search
USPC .............................. 623/1.18, 1.19
See application file for complete search history.

(56) References Cited

U.S. PATENT DOCUMENTS

| | | | | |
|---|---|---|---|---|
| 6,086,610 A * | 7/2000 | Duerig et al. | | 623/1.18 |
| 6,117,535 A * | 9/2000 | Szycher et al. | | 428/297.7 |
| 6,217,566 B1 * | 4/2001 | Ju et al. | | 604/526 |
| 6,419,694 B1 * | 7/2002 | Sandock | | 623/1.22 |
| 6,623,518 B2 | 9/2003 | Thompson et al. | | |
| 6,780,261 B2 | 8/2004 | Trozera | | |
| 6,814,746 B2 | 11/2004 | Thompson et al. | | |
| 2002/0120323 A1 | 8/2002 | Thompson et al. | | |
| 2002/0156515 A1 * | 10/2002 | Jang et al. | | 623/1.11 |
| 2004/0216814 A1 | 11/2004 | Dooley et al. | | |
| 2004/0241037 A1 | 12/2004 | Wu | | |
| 2005/0059994 A1 | 3/2005 | Walak et al. | | |
| 2005/0090844 A1 | 4/2005 | Patel et al. | | |
| 2005/0222662 A1 | 10/2005 | Thompson et al. | | |
| 2008/0119943 A1 * | 5/2008 | Armstrong et al. | | 623/23.7 |

FOREIGN PATENT DOCUMENTS

| | | |
|---|---|---|
| EP | 0 448 233 | 9/1991 |
| FR | 2 797 275 | 2/2001 |
| WO | WO 89/10421 | 11/1989 |
| WO | WO 2006/058322 | 6/2001 |
| WO | WO 2004/071350 | 8/2004 |
| WO | WO 2006/116383 | 11/2006 |

OTHER PUBLICATIONS

"Nitinol Specification Guidelines", Johnson Matthey Medical Components, accessed Sep. 21, 2011 http://jmmedical.com/resources/120/Nitinol-Specification-Guidelines.html.*
Russell, Scott M., "Nitinol Melting and Fabrication", *SMST-2000 Conference Proceedings*, pp. 1-9, XP002456650, (2001).

* cited by examiner

*Primary Examiner* — Thomas J Sweet
*Assistant Examiner* — Rebecca Preston
(74) *Attorney, Agent, or Firm* — Alana T. Bergman, Esq.

(57) ABSTRACT

According to one aspect of the present invention, a fatigue resistant stent comprises a flexible tubular structure having an inside diameter, an outside diameter, and a sidewall therebetween and having apertures extending through the sidewall. According to other aspects of the invention, processes for making a fatigue resistant stent are disclosed. According to further aspects of the invention, delivery systems for a fatigue resistant stent and methods of use are provided.

21 Claims, 8 Drawing Sheets

IMPLANT HAVING HIGH FATIGUE RESISTANCE, DELIVERY SYSTEM, AND METHOD OF USE

RELATED APPLICATIONS

This application claims the benefit of U.S. Provisional Application Ser. No. 60/840,170 filed Aug. 25, 2006 and U.S. Provisional Application Ser. No. 60/814,437, filed Jun. 16, 2006. The entire contents of both of the above applications is incorporated herein by reference in its entirety.

FIELD OF THE INVENTION

The present invention relates to an implant having high resistance to fracture when mechanically cycled at a site in a body lumen. More particularly, this invention pertains to a fatigue fracture resistant vascular implant such as a self-expanding stent.

BACKGROUND OF THE INVENTION

Stents are widely used for supporting a lumen structure in a patient's body. For example, stents may be used to maintain patency of a coronary artery, carotid artery, cerebral artery, popliteal artery, iliac artery, femoral artery, tibial artery, other blood vessels including veins, or other body lumens such as the ureter, urethra, bronchus, esophagus, or other passage.

Stents are commonly metallic tubular structures made from stainless steel, Nitinol, Elgiloy, cobalt chrome alloys, tantalum, and other metals, although polymer stents are known. Stents can be permanent enduring implants, or can be bioabsorbable at least in part. Bioabsorbable stents can be polymeric, bio-polymeric, ceramic, bio-ceramic, or metallic, and may elute over time substances such as drugs. Non-bioabsorbable stents may also release drugs over time. Stents are passed through a body lumen in a collapsed state. At the point of an obstruction or other deployment site in the body lumen, the stent is expanded to an expanded diameter to support the lumen at the deployment site.

In certain designs, stents are open-celled or close-celled cylindrical structures that are expanded by inflatable balloons at the deployment site. This type of stent is often referred to as a "balloon expandable" stent. Stent delivery systems for balloon expandable stents are typically comprised of an inflatable balloon mounted on a multi lumen tube. The stent delivery system with stent crimped thereon can be advanced to a treatment site over a guidewire, and the balloon inflated to expand and deploy the stent.

Other stents are so-called "self expanding" stents and do not use balloons to cause the expansion of the stent. An example of a self-expanding stent is a tube (e.g., a coil tube, a mesh tube, or an open-celled tube) made of an elastically deformable material (e.g., a superelastic material such a nitinol). This type of stent is secured to a stent delivery device under tension in a collapsed state. At the deployment site, the stent is released so that internal tension within the stent causes the stent to self-expand to its enlarged diameter.

Other self-expanding stents are made of so-called shape-memory metals. Such shape-memory stents experience a phase change at the elevated temperature of the human body. The phase change results in expansion from a collapsed state to an enlarged state.

A very popular type of self expanding stent is an open-celled tube made from superelastic nitinol, for example, the Protégé GPS stent from ev3, Inc. of Plymouth, Minn. Open or closed cell tube stents are commonly made by laser cutting of tubes, or cutting patterns into sheets followed by or preceded by welding the sheet into a tube shape, and other methods. Another delivery technique for a self expanding stent is to mount the collapsed stent on a distal end of a stent delivery system. Such a system can be comprised of an outer tubular member and an inner tubular member. The inner and outer tubular members are axially slideable relative to one another. The stent (in the collapsed state) is mounted surrounding the inner tubular member at its distal end. The outer tubular member (also called the outer sheath) surrounds the stent at the distal end.

Prior to advancing the stent delivery system through the body lumen, a guide wire is first passed through the body lumen to the deployment site. The inner tube of the delivery system is hollow throughout at least a portion of its length such that it can be advanced over the guide wire to the deployment site. The combined structure (i.e., stent mounted on stent delivery system) is passed through the patient's lumen until the distal end of the delivery system arrives at the deployment site within the body lumen. The deployment system and/or the stent may include radiopaque markers to permit a physician to visualize positioning of the stent under fluoroscopy prior to deployment. At the deployment site, the outer sheath is retracted to expose the stent. The exposed stent is free to self-expand within the body lumen. Following expansion of the stent, the inner tube is free to pass through the stent such that the delivery system can be removed through the body lumen leaving the stent in place at the deployment site.

In prior art devices, the stent may prematurely deploy as the outer tube is retracted accidentally. Further, once the stent has been deployed, subsequent adjustment of the stent deployment location can be difficult because re-sheathing typically cannot be readily accomplished. To overcome some of these problems some stent delivery systems are comprised of interlocks on the stent and on the inner member. See for example U.S. Pat. No. 6,814,746 to Thompson et. al., entitled "Implant Delivery System With Marker Interlock", and U.S. Pat. No. 6,623,518 to Thompson et. al., entitled "Implant Delivery System With Interlock", the contents of both included herein in their entirety by reference.

A common problem with stents properly deployed in some vessels is that the stents fracture over time. Problems secondary to stent fracture can include pain, bleeding, vessel occlusion, vessel perforation, high restenosis rate, non-uniform drug delivery profile, non-even vessel coverage and other problems, and re-intervention may be required to resolve the problems. Stents are commonly designed for high pulsatile fatigue life, i.e., for resistance to fracture under the diametrical pulsatile movement in an otherwise static blood vessel, as may be appropriate for some implantation sites. Stents however are not usually designed for resistance to fracture under in-patient loading conditions other than pulsatile, as is appropriate for other implantation sites. Stents at implantation sites such as the popliteal artery, iliac artery, femoral artery, tibial artery, and others can suffer from large amounts of axial, bending, or torsional cyclic loading and from large amounts of bending and twisting. It is believed that the high fracture rate of stents implanted in these locations is due to stent designs and stent material mechanical properties that are incapable of withstanding the high mechanical forces applied to the stents by patient activity over and above those forces produced by the beating heart.

Attempts have been made to improve the fatigue resistance of materials used for implantable medical devices. In U.S. Pat. No. 6,780,261 Trozera proposes use of malleable, recrystallized materials. This approach is unlikely to be suitable for many self expanding stent applications where malleability should be low. In Wu (U.S. Patent Application Publication Number 2004/0241037), Dooley (U.S. Patent Application Publication Number 2004/0216814), and Patel (U.S. Patent Application Publication Number 2005/0090844) the use of cold working or pre-straining is disclosed, and in Walak (U.S. Patent Application Publication Number 2005/0059994) use of a stabilized martensitic surface is disclosed. However, one cannot always uniformly apply these approaches to the surface of an implant because of limiting factors such as access and geometry.

What is needed is a stent that can be easily manufactured and that will survive without fracture when implanted in locations that experience high mechanical forces produced by patient activity over and above those forces produced by the beating heart.

SUMMARY OF THE INVENTION

In one embodiment, an implant comprising a nickel titanium alloy may be heat set by (a) restraining the implant on a mandrel having a first diameter and annealing the implant within a first temperature range; (b) after (a), restraining the implant on a mandrel having a second diameter and annealing the implant within a second temperature range that is higher than the first temperature range; and (c) after (b), annealing the implant within a third temperature range that is lower than the second temperature range and while the implant is restrained on a mandrel. In some embodiments, the second diameter is larger than the first diameter. Further disclosed are implants made according to the methods disclosed herein, and delivery devices that include a delivery catheter and an implant heat set according to methods disclosed herein.

In another embodiment an implant comprising a nickel titanium alloy has a bend-rotate fatigue life of at least 1 million cycles to failure. The cycles to failure is the number of full rotations made by the implant before the implant breaks.

In another embodiment, an implant is disclosed that has a nickel titanium alloy, and a kink radius of no greater than 0.195 inches, wherein the kink radius is half the distance between the implant unkinked ends held parallel to each other when the implant is kinked by bending. The implant may have a kink radius of no greater than 0.189 inches, 0.171 inches, or 0.165 inches.

In some embodiments, a delivery device includes an implant disclosed herein and a catheter for delivery of the implant.

BRIEF DESCRIPTION OF THE DRAWINGS

The above and further advantages of the invention may be better understood by referring to the following description in conjunction with the accompanying drawings in which.

DETAILED DESCRIPTION

With reference now to the various drawing figures a description is provided of embodiments that are examples of how inventive aspects in accordance with the principles of the present invention may be practiced. It is to be understood that both the foregoing general description and the following detailed description are exemplary and explanatory only and are not restrictive of the broad inventive aspects disclosed herein. It will also be appreciated that the inventive concepts disclosed herein are not limited to the particular stent configurations disclosed herein, but are instead applicable to any number of different stent configurations.

Figure 1:
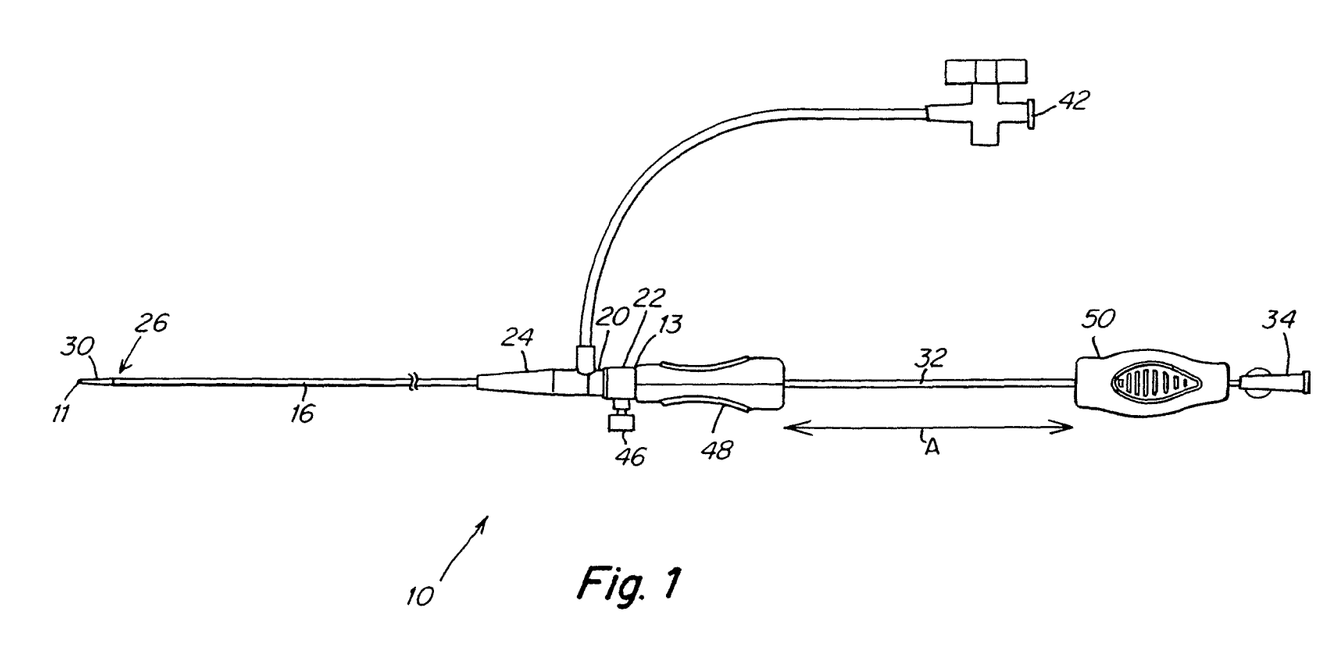
FIG. 1 is a side elevation view of one embodiment of a stent delivery system comprised of a fatigue resistant stent having features that are examples of inventive aspects in accordance with the principles of the present disclosure.
Figure 2:
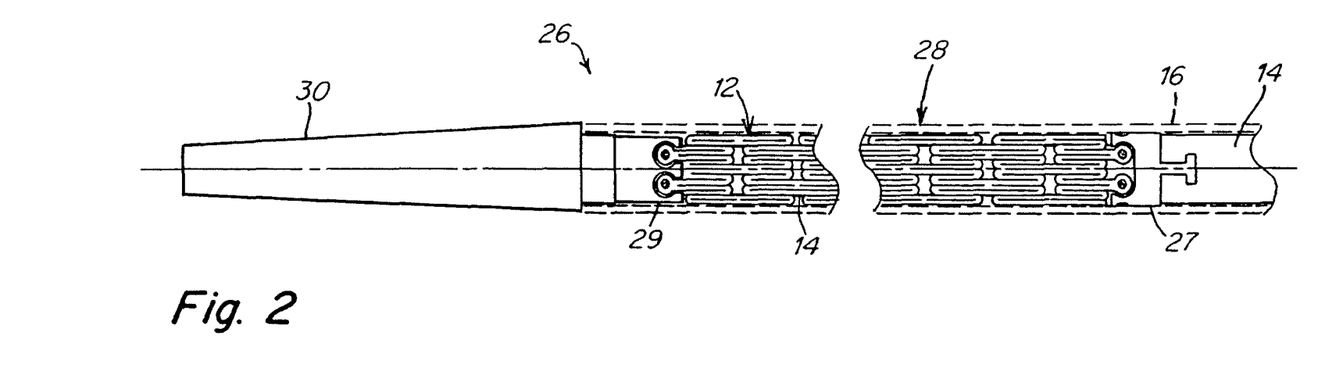
FIG. 2 is an enlarged view of the distal end of the system of FIG. 1 with an outer sheath shown in phantom line.
Figure 3:
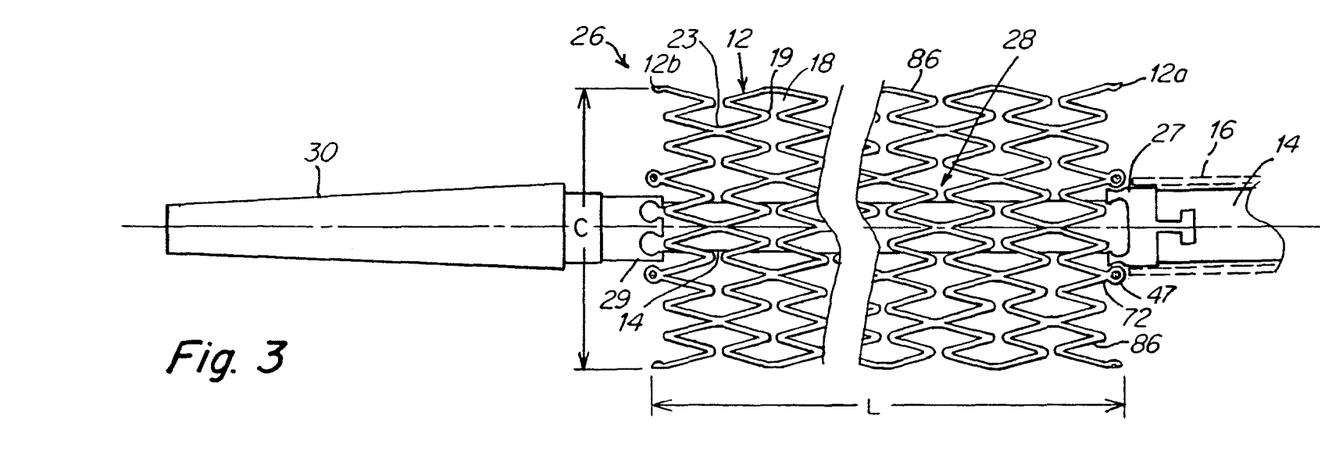
FIG. 3 is the view of FIG. 2 with the outer sheath retracted.

FIGS. 1-3 show an over-the-wire stent delivery system 10 having distal and proximal ends 11, 13, inner member 14, and retractable outer sheath 16 that slides over inner member 14. Stent mounting location 26 is located adjacent distal end 11 of system 10. Stent 12 (visible in FIGS. 2 and 3) is carried at stent mounting location 26 of stent delivery system 10 in a collapsed (or reduced diameter) state. Stent 12 mounts over inner member 14 and is covered by sheath 16 so as to be retained in the collapsed state (see FIG. 2). Stent 12 is released (i.e., deployed) by retracting sheath 16 to uncover or expose stent 12 (see FIG. 3). System 10 includes proximal interlock structure 27 that prevents stent 12 from prematurely deploying, one or more mid interlock structures 28 that assist with uniform stent deployment and with stent loading, and optional distal interlock structure 29 that assists with uniform stent deployment and with stent loading. Upon release of stent 12 from stent delivery system 10, stent 12 expands to an enlarged diameter to abut against the walls of the patient's lumen in order to support patency of the lumen. The expansion of stent 12 also causes stent 12 to disengage from interlock structures 27, 28 and 29.

System 10 is configured to be advanced through the patient's body lumen. In use, system 10 may be sufficiently long for distal end 11 to be placed at the deployment site in the patient's body lumen with proximal end 13 remaining external to the patient's body for manipulation by an operator.

Sheath 16 of system 10 may have a variety of different constructions. In certain embodiments, the sheath has a tubular construction of braid-reinforced polyester adapted to resist kinking and to transmit axial forces along the length of sheath 16. Sheath 16 may be constructed so as to have varying degrees of flexibility along its length. Inner member 14 of system 10 is relatively flexible and can be made of a polymeric material such as nylon. In certain embodiments, inner member 14 has a tubular configuration and defines a lumen that extends through an entire length of inner member 14. This type of configuration allows the system to be passed over a guidewire for guiding the system to a desired deployment location. However, in other embodiments, inner member 14 can have a solid, non-tubular configuration.

Distal end 11 of system 10 includes a tapered and flexible distal tip member 30 that is sufficiently flexible to permit advancement of stent deployment system 10 through the patient's lumen while minimizing trauma to the walls of the patient's lumen. Tip 30 is connected to inner member 14 adjacent stent mounting location 26. Proximal end 13 of system 10 includes manifold housing 20 connected to lock housing 22. Sheath 16 connects to manifold housing 20. Strain relief jacket 24 surrounds sheath 16 adjacent its connection to housing 20 to provide strain relief for sheath 16. Inner member 14 passes through both manifold housing 20 and lock housing 22. Outer reinforcing member 32 surrounds and is bonded to inner member 14 adjacent proximal end 13 of system 10. Reinforcing member 32 may be made of a relatively rigid material such as stainless steel. Port housing 34 is bonded to reinforcing member 32. Port housing 34 has a bore aligned with an inner lumen of inner member 14 and functions to facilitate access to the inner lumen.

Manifold housing 20 carries admission port 42 for injecting a contrast media into the interior of manifold housing 20. The interior of manifold housing 20 may be in fluid communication with a passage between inner member 14 and sheath 16. In use, the contrast media can be directed from the passage into the patient's body lumen through discharge ports (not shown).

Lock housing 22 carries a threaded locking member (or lock nut) 46 which can be turned to engage reinforcing member 32. Lock nut 46 selectively permits and fixes axially movement between the inner member and the sheath. Relative movement between the inner member and the sheath is permitted to define a transport position and a deploy position of the system 10.

First and second handles 48, 50 are secured to lock housing 22 and reinforcing member 32, respectively. In the transport position, handles 48 and 50 are spaced apart and sheath 16 covers stent mounting location 26 to prevent premature deployment of stent 12. When handles 48 and 50 are moved toward each other, sheath 16 slides rearwardly or proximally relative to inner member 14. In other words, relative axial movement between handles 48 and 50 (represented by arrow A) results in relative axial movement between inner member 14 and sheath 16. In particular, sheath 16 slides rearwardly from the transport position to the deploy position to fully expose stent mounting location 26 and permit stent 12 to freely expand toward its fully expanded diameter. After such expansion, the stent delivery system can be proximally withdrawn through the expanded stent and removed.

Delivery system 10 may be equipped with an interlock configuration (e.g., interlock structures 27, 28, or 29 of FIGS. 2 and 3) that constrains relative axial movement between stent 12 and inner member 14 until after sheath 16 has been fully retracted. For example, when stent 12 is mounted on inner member 14 and restrained in the compressed orientation by sheath 16, a proximal interlock geometry located at a proximal end 12a of stent 12 interlocks with proximal interlock geometry 27 adjacent the stent mounting location 26, a mid interlock geometry located at one or more locations along length of stent 12 interlocks with a mid interlock geometry 28 adjacent the stent mounting location 26, and a distal interlock geometry located at a distal end 12b of stent 12 interlocks with a distal interlock geometry 29 adjacent the stent mounting location 26. The interlock geometries remain interlocked to constrain axial movement of stent 12 until after the sheath has been retracted beyond a predetermined location (e.g., the proximal-most end 12a of stent 12). When sheath 16 has been retracted beyond the predetermined location, the interlock geometry of stent 12 is allowed to expand. As the interlock geometry of the stent expands, the interlock geometry of stent 12 disengages from the proximal, mid, and distal interlock geometries thereby allowing inner member 14 of system 10 to be moved axially relative to the stent without interference from the interlock geometries. Stent interlocks are further described in co-pending U.S. patent application No. 60/800, 106 entitled "IMPLANT AND DELIVERY SYSTEM WITH MULTIPLE MARKER INTERLOCKS" and filed on May 12, 2006, U.S. patent application Ser. No. 10/982,537 entitled "IMPLANT DELIVERY SYSTEM WITH MARKER INTERLOCK" filed on Nov. 4, 2004, U.S. Pat. No. 6,814,746 entitled "STENT DELIVERY SYSTEM WITH RETAINER" which issued on Jun. 28, 2004, U.S. Pat. No. 6,623,518 entitled "IMPLANT DELIVERY SYSTEM WITH INTERLOCK" which issued on Mar. 25, 2003, and U.S. patent application Ser. No. 09/954,555 entitled "IMPLANT DELIVERY SYSTEM WITH INTERLOCK" which was filed on Sep. 17, 2001, each of which is incorporated by reference in their entirety herein.

Stent 12 has a length L and a circumference C, and includes a plurality of struts 86 (i.e., reinforcing members). At least some of the struts 86 have free terminal ends 72 that define proximal and distal ends 12a and 12b of the stent 12. The stent 12 includes interlock geometry in the form of enlargements 47 positioned at the free terminal ends of the struts 86. As shown in FIG. 3, the enlargements are circular enlargements. It will be appreciated that other shapes and interlock configurations could also be used. The enlargements 47 project outwardly from the struts 86 in a circumferential direction (i.e. in a direction coinciding with the circumference C of the stent 12). In certain embodiments, the stent 12 can be manufactured by cutting (e.g., laser cutting) the various features from a solid tube of material. When manufactured by this technique, the enlargements 47 do not project radially beyond an inner and outer diameter of the stent.

Figure 4A:
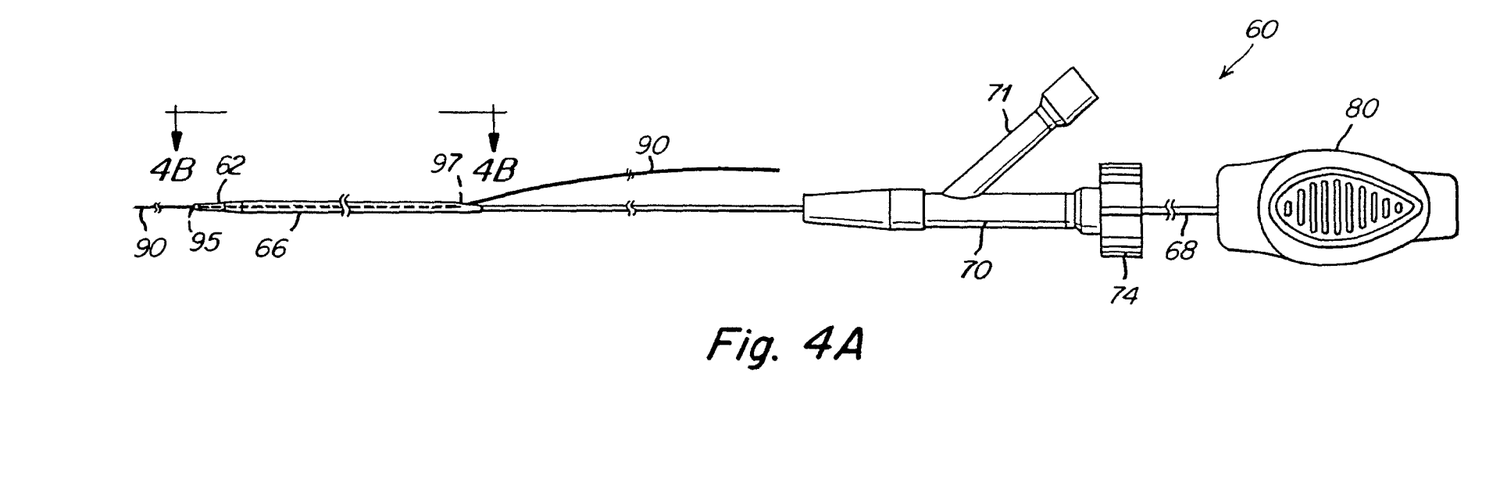
FIGS. 4A and 4B are side elevation views of an alternate embodiment of a stent delivery system comprised of a fatigue resistant stent.
Figure 4B:
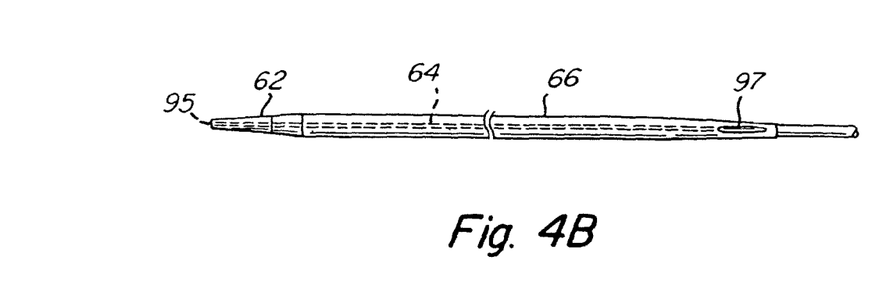

FIGS. 4A and 4B illustrate an alternate embodiment of a stent delivery system. Rapid exchange stent delivery system 60 includes sheath 66 and inner member 64 disposed within sheath. Manifold housing 70 is coupled to sheath 66. Housing 70 includes side arm 71 and locking member 74. Push wire 68 is coupled to inner member 64 at its distal end and to handle 80 at its proximal end. Inner member 64 and sheath 66 are axially slideable relative to one another. Push wire 68 and housing 70 are used to facilitate movement of inner member 64 relative to sheath 66. Locking member 74 can be operated to couple housing 70 to push wire 68 in order to slide both sections along together. Relative movement between the inner member and the sheath is permitted to define a transport position and a deploy position of the system 60. Stent (not shown) mounts over inner member 64 and is covered by sheath 66 so as to be retained in the collapsed state. The stent is released (i.e., deployed) by retracting sheath 66 to uncover or expose stent. System 60 includes proximal interlock structure (not shown) that prevents stent from prematurely deploying, one or more mid interlock structure (not shown) that assist with uniform stent deployment and with stent loading, and one or more distal interlock structure (not shown) that assist with uniform stent deployment and with stent loading. Upon release of stent from stent delivery system 60, stent expands to an enlarged diameter to abut against the walls of the patient's lumen in order to support patency of the lumen.

The expansion of stent also causes stent to disengage from proximal, mid, and distal interlock structures.

Sheath 66 may be made of kink resistant extruded polymer tubing with adequate strength and lubricity for unsheathing a stent. Polymers such as nylon, PEBAX, polyethylene, or polyester may be used. Alternatively, thermoset polymers such as polyimide or braid reinforced polyimide may be used. In some embodiments the distal portion of the outer member is transparent to allow inspection of the stent within. Inner member 64 may be made of flexible kink resistant polymer such as metallic braid reinforced polyimide, although polymers such as nylon, PEBAX, polyethylene, or polyester may be used. Push wire 68 may be constructed of metal. In certain embodiments the proximal portion of push wire is comprised of stainless steel tubing and the distal portion of push wire 68 is comprised of metal wire. This combination provides adequate column strength throughout, good bending resistance proximally, and good bending flexibility distally. Housing 70 and locking member 74 may be comprised of polycarbonate, polystyrene, or other materials, and a sealing gland (not shown) may be used in cooperation with housing 70 and locking member 74 to effect a fluid seal and/or mechanical lock between housing, locking member, and push wire 68 as is well known in the art. Handle 80 may be comprised of polycarbonate, polystyrene, nylon, or other materials. Alternate materials for these components are generally well known in the art can be substituted for any of the non-limiting examples listed above provided the functional requirements of the component are met.

Guidewire 90 has a nominal outer diameter of 0.010"-0.038", such as 0.014". Inner member 64 is dimensioned to allow low friction passage of guidewire 90 within guide wire lumen 95 and through RX port 97. Guide wire lumen length can vary widely, for example within the range from 5 cm to 50 cm in length. In certain embodiments guide wire lumen 95 is approximately 30 cm in length. Sheath maximum outside diameter can range from about 10 Fr to about 3 Fr. A sheath outside diameter of about 5 Fr is desirable for compatibility with currently popular guide catheter (not shown) dimensions. Sheath length can be varied to suit the application of interest. Sheath lengths of 40 cm-200 cm have been found desirable. In certain embodiment a sheath length of about 145 cm has been used.

Figure 5:
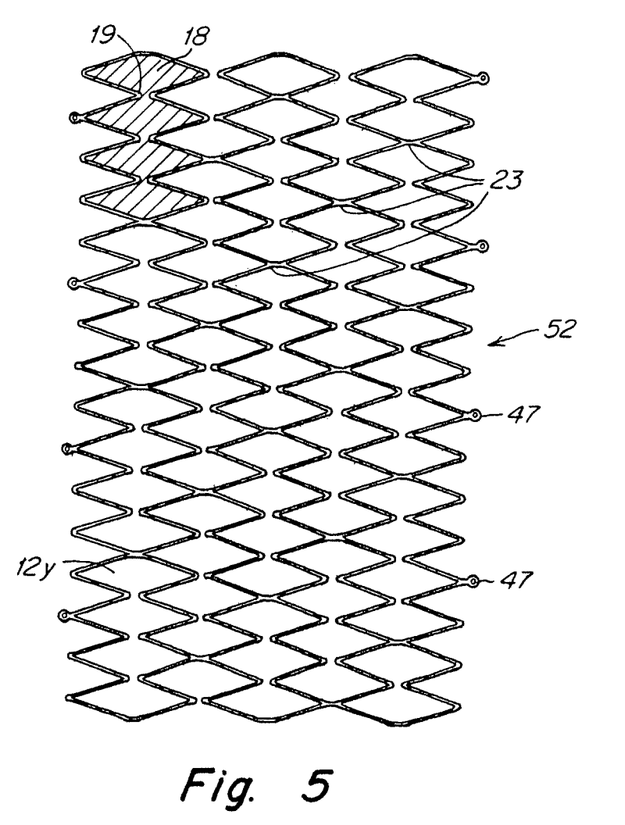
FIGS. 5 and 6 illustrate plan views of exemplar fatigue resistant stent embodiments. The stents are shown expanded and the stent structures are shown cut longitudinally and laid flat.

FIGS. 5-9 illustrate a variety of fatigue resistant stents having different characteristics. FIG. 5 illustrates expanded stent 52 similar to stent 12 shown in FIGS. 2, 3, and 4 and having enlarged ends 47 and mid-stent retainer pockets 12y that both interlock with interlock geometry of a delivery catheter. Stent 52 has cells 18, each cell comprised of six strut bend regions 19. Stent cells 18 are connected to adjacent cells 18 by means of interconnection regions 23. Interconnection regions 23 are not aligned opposite to one another in adjacent cells 18 with regards to the lengthwise axis of the stent. Interconnection regions 23 have lengths along the length of stent 52. Interconnection region 23 length is between approximately 0.5% and 5% of cell length with respect to the axial direction of stent length L. In certain embodiments interconnection region 23 length is between 0.5% and 3% of cell length. In some embodiments interconnection region 23 length is between 0.5% and 1.5% of cell length. Stent 52 may be comprised of metal, polymer, ceramic, permanent enduring materials, or bioabsorbable materials. Bioabsorbable stents 52 can be polymeric, bio-polymeric, ceramic, bio-ceramic, or metallic, or may be made from combinations of these materials. Bioabsorbable and non-bioabsorbable stents 52 may elute over time substances such as drugs.

Figure 5A:
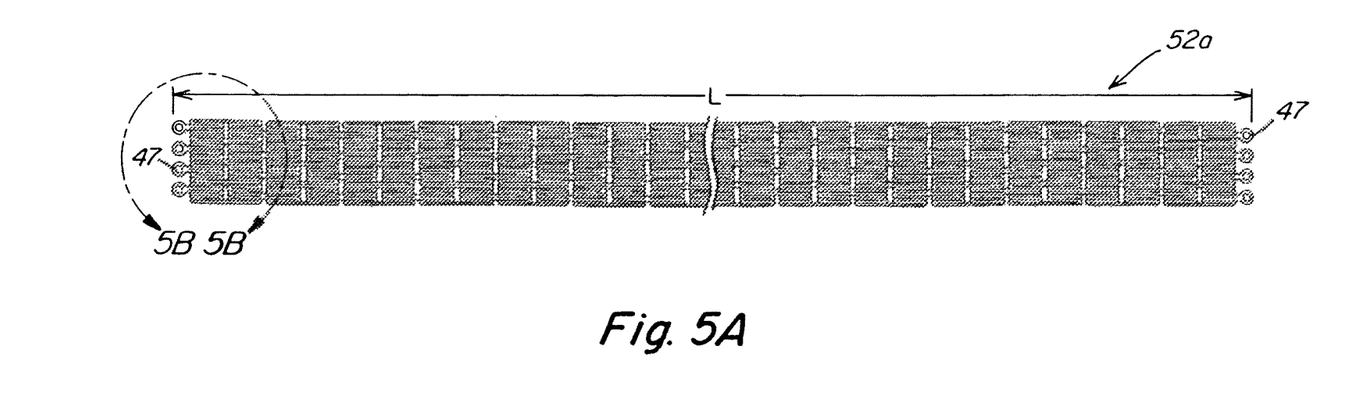
FIGS. 5A and 5B illustrate plan views of exemplar fatigue resistant stent embodiments. The stents are shown unexpanded and the stent structures are shown cut longitudinally and laid flat.
Figure 5B:
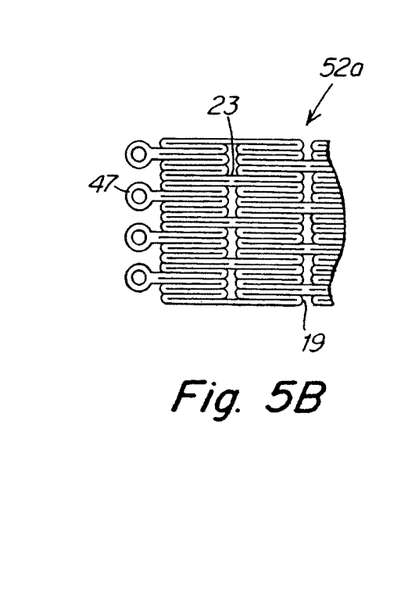

FIGS. 5A and 5B illustrate unexpanded stent 52a. Stent 52a is similar to stent 52 and has enlarged ends 47 and mid-stent retainer pockets 12y that both interlock with interlock geometry of a delivery catheter. Stent 52 has cells 18 (not shown), each cell comprised of six strut bend regions 19. Stent cells 18 are connected to adjacent cells 18 by means of interconnection regions 23. Interconnection regions 23 are not aligned opposite to one another in adjacent cells 18 with regards to the lengthwise axis of the stent. Interconnection regions 23 have lengths along the length of stent 52. Interconnection region 23 length is between approximately 0.5% and 5% of cell length with respect to the axial direction of stent length L. Stent 52a may have the specific dimensions as delineated in FIGS. 5A and 5B, and all such dimensions may be laser cut without any finishing. Stent 52a is finished by processes such as microgrit blasting to remove slag, electropolishing to remove stent material having heat affected zone and other imperfections, and surface passivation to render surface of stent 52a more resistant to corrosion. The dimensions shown in the figures are merely illustrative and should not be considered limitations of the invention.

Figure 6:
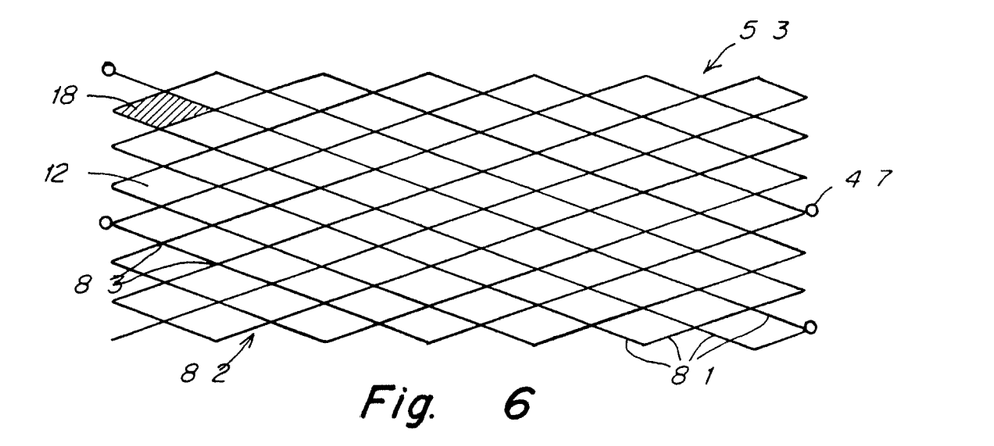

FIG. 6 illustrates expanded fatigue resistant stent 53 comprised of mesh 82. Mesh 82 may be comprised of intertwined, joined, or non-woven filaments 81. In some embodiments filaments 81 are braided, woven, knitted, circular knitted, compressed, or otherwise fabricated into a porous mesh structure having cells 18p. Filaments 81 may be joined at one or more crossings 83 by sintering, bonding, soldering, fusing, welding, or other means. In other embodiments mesh 82 is comprised of a tube having cells 18p formed through the wall of the tube, by means such as laser cutting, electrochemical etching, grinding, piercing, or other means. In some embodiments mesh 82 is formed by electroforming. Stent 53 may have one or more enlarged ends 47. Enlarged ends 47 may be formed integral to the stent, for example in a stent made using electroforming manufacturing methods, or may be joined to stent 53, for example in a stent made by braiding, using methods known in the art such as welding or fusing. Stent 53 has one or more retainer pockets 12p. One or more enlarged end 47 and retainer pocket 12p together with interlocking structure of a stent delivery catheter may comprise an interlocking stent delivery system. Stent 53 may be comprised of metal, polymer, ceramic, permanent enduring materials, or bioabsorbable materials. Bioabsorbable stents 53 can be polymeric, bio-polymeric, ceramic, bio-ceramic, or metallic, or may be made from combinations of these materials. Bioabsorbable and non-bioabsorbable stents 53 may elute over time substances such as drugs.

Figure 7:
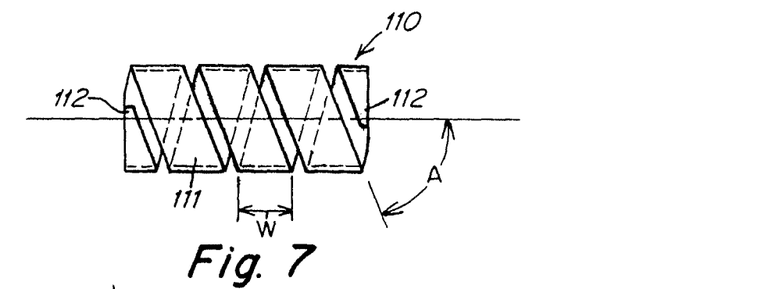
FIGS. 7 and 8 illustrate side views of exemplar fatigue resistant stent embodiments. The stents are shown expanded.
Figure 8:
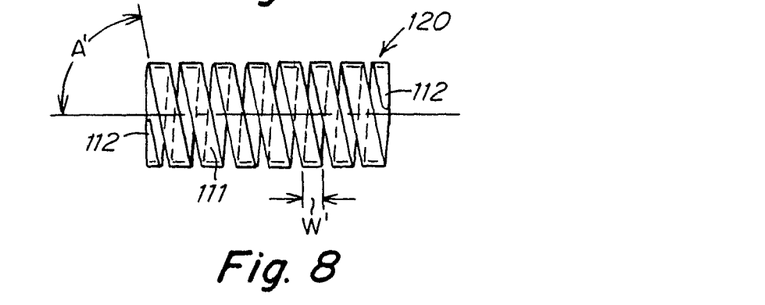

FIGS. 7 and 8 illustrate alternate fatigue resistant stent embodiments. Coil stents 110, 120 are comprised of ribbon 111 having widths W and W', respectively, wound into a hollow cylinder form and having a wind angles A and A', respectively. Stent 120 is comprised of ribbon 111 having width W' less than width W of ribbon in stent 110, and having wind angle A' greater than wind angle A of ribbon in stent 110. Ends 112 of ribbon may be rounded to prevent tissue damage or tissue irritation in vicinity of ends 112 when stent 110, 120 is implanted into a patient. Ribbon 111 may be comprised of metal, polymer, ceramic, permanent enduring materials, or bioabsorbable materials. Bioabsorbable ribbons 111 can be polymeric, bio-polymeric, ceramic, bio-ceramic, or metallic, or may be made from combinations of these materials. Bioabsorbable and non-bioabsorbable ribbons 111 may elute over time substances such as drugs.

Figure 9:
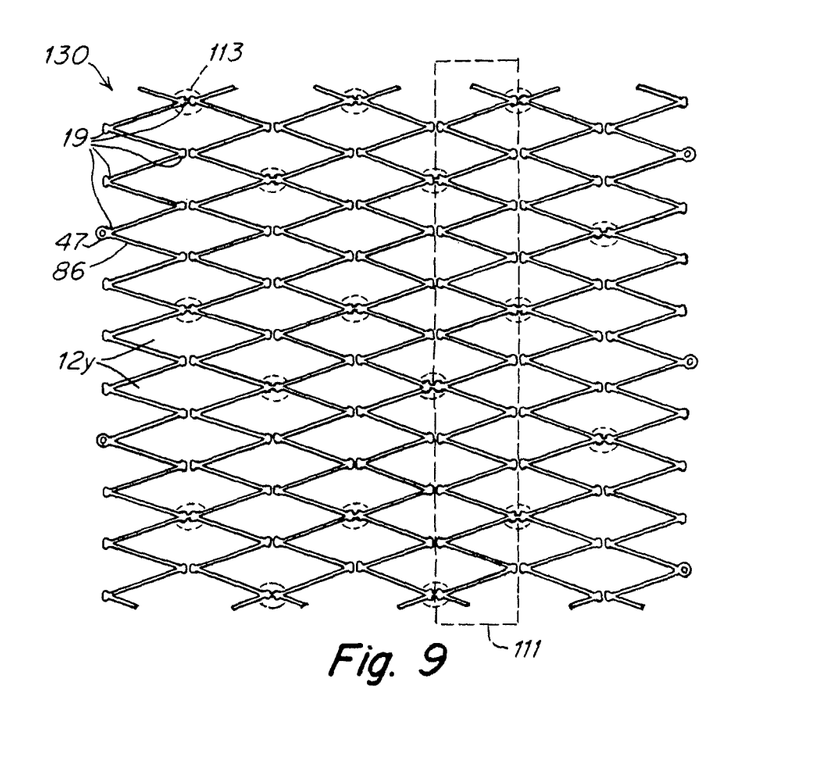
FIG. 9 illustrates a plan view of an exemplar fatigue resistant stent. The stent is shown expanded and the stent and interlock structures are shown cut longitudinally and laid flat.

Ribbon 111 is comprised of an expandable architecture 130 also suitable for use a coiled ribbon illustrates in FIGS. 7 and 8. One example of an expandable architecture 130 is illustrated in FIG. 9. Ribbon 111 is shown partially expanded and the ribbon and interlock structures are shown cut longitudinally and laid flat. Expandable architecture 130 is comprised of enlarged ends 47, mid-stent retainer pockets 12y, struts 86, bend regions 19, and one or more interconnection regions 113. Struts 86 and bend regions 19 together form a zig-zag shaped expandable architecture of ribbon 111. Other expandable architectures are contemplated for expandable architecture of ribbon 111 such as various serpentine or meandering paths. Interconnection regions 113 join adjacent ribbons 111 and can fracture in a controlled manner such that when fractured interconnection regions 113 no longer join adjacent ribbons 111.

Figure 10:
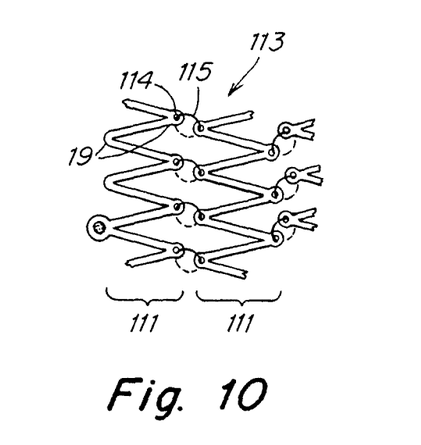
FIG. 10 illustrates a plan view of a section of an exemplar fatigue resistant stent. The stent is shown partially expanded and the stent segment and interlock structures are shown cut longitudinally and laid flat.

FIG. 10 illustrates interconnection regions 113 that comprise holes 114 in bend regions 19 and one or more strand 115. Strand 115 passes through holes 114 along a pathway that joins together adjacent ribbons 111a and 111b. In the example illustrated in FIG. 10, strand 115 passes through holes 114 in adjacent bend regions 19 and forms a closed loop. Many other strand pathways are possible, such as a single strand 115 passing through holes 114 of multiple bend regions 19, and other configurations as are apparent to those skilled in the art. Strand 115 is comprised of a material that fractures in a controlled manner, and may be formed of biodegradable suture or other materials. In an alternate embodiment interconnection regions 113 are comprised of a biodegradable coupling such as a tube that surrounds bend regions 19. In another alternate embodiment, interconnection regions 113 are comprised of a biodegradable rivet that passes through holes 114 in adjacent bend regions 19.

Figure 11:
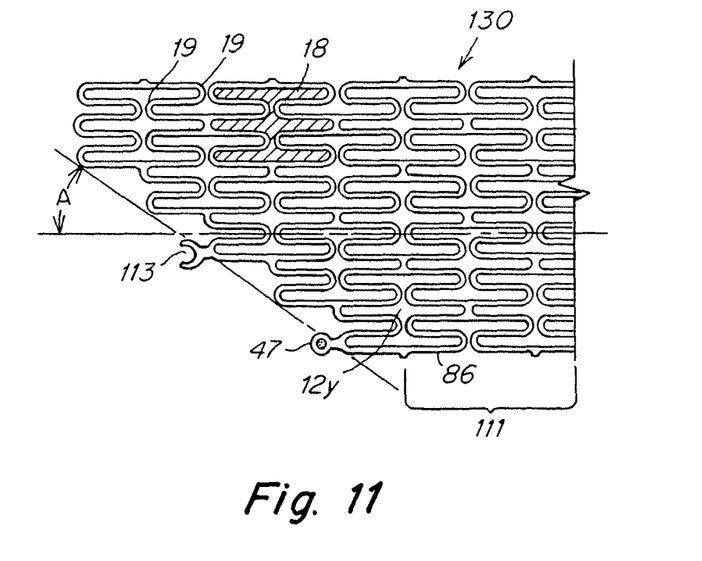
FIG. 11 illustrates a plan view of a section of an exemplar fatigue resistant stent. The stent is shown partially expanded and the stent segment and interlock structures are shown cut longitudinally and laid flat.

FIG. 11 illustrates another example of an expandable architecture 130. A fractional portion of ribbon 111 is shown partially expanded and the ribbon and interlock structures are shown cut longitudinally and laid flat. Expandable architecture 130 is comprised of cells 18, enlarged ends 47, mid-stent retainer pockets 12y, struts 86, bend regions 19, and one or more interconnection regions 113. Struts 86 and bend regions 19 together form a cellular expandable architecture of ribbon 111 with similarities to the cellular structures described in connection with at least FIGS. 2, 3 and 5. Interconnection regions 113 join adjacent ribbons 111 and can fracture in a controlled manner such that when fractured, interconnection regions 113 no longer join adjacent ribbons 111. Interconnection regions 113 may be comprised of expanded ends 116 and receiver ends 117, interdigitating ends 118, or other structures.

Coil stent architectures which may be incorporated as part of fatigue resistant stents are further described in U.S. patent application No. 60/674,859 entitled NON-FRACTURE STENT DESIGN which was filed on Apr. 25, 2005, and subsequently also filed as PCT/US06/15596 entitled CONTROLLED FRACTURE CONNECTIONS FOR STENT filed on Apr. 25, 2006, and each which is incorporated by reference in their entirety herein.

The invention contemplated is suitable for stents in addition to those cited herein. For example, fatigue resistant stents may comprise tapered stents, flared stents, braided stents, bifurcation stents, and other stents as are known in the art. Tapered stents generally have a proximal end of one diameter and a distal end of a second diameter (typically a smaller diameter). Flared stents generally have a short tapered portion at the proximal end of a cylindrical stent, where the flared section is larger in diameter than the cylindrical portion. Braided stents are typically comprised of a tube manufactured by using a braiding method. An example of a braided stent is the Wallstent, sold by Boston Scientific, Natick, Mass. Bifurcation stents are placed in a patient where a vessel branches. Bifurcation stents are generally comprised of a single stent portion that branches into two stent portions and appears similar to a Y-fitting used to connect one piece of tubing to two pieces of tubing.

In certain embodiments fatigue resistant stents are comprised of superelastic material, such as binary Nitinol alloys with nominal composition of 50-52 atomic percent nickel and the balance of the material comprised of titanium. In some embodiments the superelastic material is comprised of ternary or quaternary nitinol alloys having a nickel/titanium ratio of 1/1 to 1/1.3. In certain embodiments the superelastic material is comprised of binary Nitinol tubing having a composition of about 50.8 atomic percent nickel (about 56 weight percent nickel) and the balance of the material comprised of titanium with small amounts of impurities, the overall composition, structure, and properties falling within the requirements of ASTM Standard F-2063-05. Such material is available under order number SE508 from NDC Corporation of Fremont, Calif. In certain embodiments the superelastic material is comprised of binary Nitinol tubing having a composition of about 50.8 atomic percent nickel (about 56 weight percent nickel) and the balance of the material comprised of titanium with small amounts of impurities.

Figure 12:
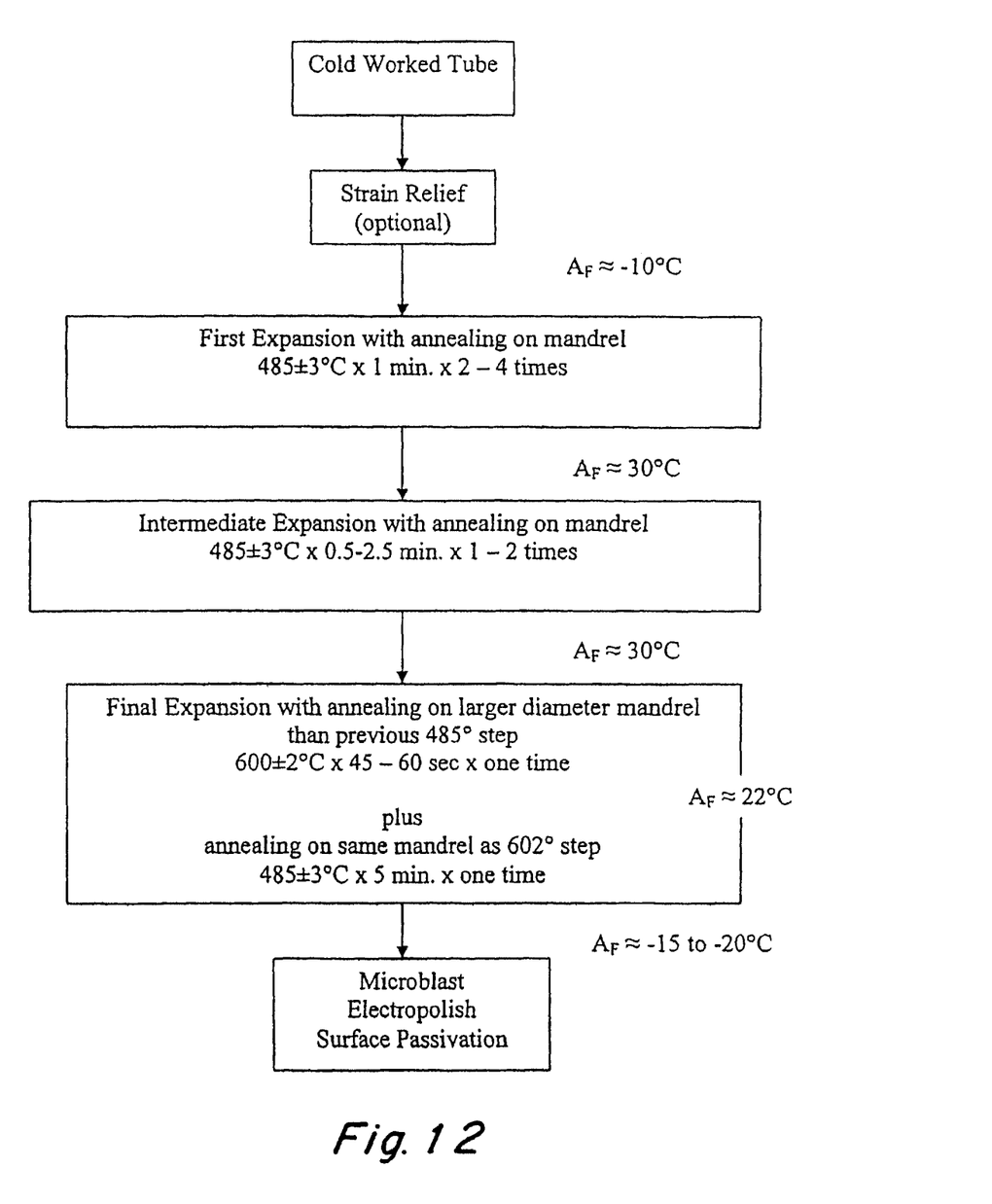
FIG. 12 illustrates schematically an exemplar annealing process for a fatigue resistant stent.

In some embodiments, Nitinol is heat treated to improve the fatigue life of the material. One example of a manufacturing process for a 6 mm fatigue resistant stent is illustrated in FIG. 12 and described below. Cold worked Nitinol tubing (approximately 40% cold work and approximate $A_F$ of $-10°$ C.) having an outside diameter of 0.060" and a wall thickness of 0.0105" is optionally stress annealed and then apertures may be laser cut through the wall of the tubing. The cut tube is expanded by forcing the cut tube onto a 2.0 mm outside diameter mandrel having a tapered end (first expansion). After first expansion the tubing is annealed on the 2.0 mm mandrel at 485±3° C. for 1 minute after which the $A_F$ will be approximately +30° C. Intermediate expansions are carried out by forcing the cut tube onto successive 3.0 mm, 4.0 mm, and 5.0 mm outside diameter mandrels, each having a tapered end, with successive anneals of the tubing on each of the 3.0 mm, 4.0 mm, and 5.0 mm mandrels at 485±3° C. for 1 minute for each anneal. After the intermediate expansions the $A_F$ will be approximately +30° C. Final expansion is carried out by forcing the cut tube onto a 6.0 mm outside diameter mandrel having a tapered end and is followed by annealing the tubing on the 6.0 mm mandrel at 600±2° C. for 45-60 seconds and then at 485±3° C. for 5 minutes on the same 6.0 mm mandrel. After the 600° C. anneal the $A_F$ will be approximately +22° C. and after the final 485° C. anneal the $A_F$ will be approximately $-15°$ C. to $-20°$ C. The 485° C. first and intermediate anneals will shape set the Nitinol and raise the austenite finish temperatures ($A_F$) to a level unsuitable for use as a stent in a patient. The 600° C. anneal will dissolve nickel rich precipitates in the material and the resultant more homogeneous material will be less prone to fatigue fracture. The 600° C. anneal will also lower the $A_F$ somewhat. The final 485° C. anneal will shape set the Nitinol and further lower the $A_F$ to a level suitable for use as a stent in a patient. In certain embodiments, Nitinol tubing having a composition of about 50.8 atomic percent nickel (about 56 weight percent nickel) and the balance of the material comprised of titanium, after being subjected to the heat treatment described above, will have an upper plateau stress of 355±7.2 MPa, a lower plateau stress of 104±7.2 MPa, an ultimate tensile stress of 1,088±51 MPa, and an elongation of 15.4±2.2% (measured in tension).

Properties of stents can be measured in many ways. Particularly useful measurements include kink radius, flexural peak load, flexural modulus, and bend-rotate fatigue life.

Kink radius is measured using the following method. A calibrated ruler is placed on a table and a stent is held by the ends with the long axis of the stent parallel to the table surface and parallel to the ruler. The stent is bent until it kinks. With the un-kinked ends of the stent parallel to each other the distance between the un-kinked parallel ends of the stent is measured using the ruler. The measurement is divided in half to arrive at the stent kink radius. The stents are preconditioned to 37° C. for at least one hour prior to kink testing, and are tested at ambient conditions.

Flexural peak load and flexural modulus are measured by 3-point bending using the following method. A stent is loaded into a fixture having 3 mandrels oriented parallel to each other and at 90° to the long axis of the stent. Two of the mandrels are aligned horizontally below the stent and the third mandrel is aligned above the stent and midway between the two mandrels below the stent. The separation of the mandrels (span length) below the stent is prescribed according to the table below.

| Stent Length (mm) | Span Length (mm) |
| --- | --- |
| 10-14 | 6 |
| 15-19 | 11 |
| 20-24 | 16 |
| 25-35 | 21 |
| >35 | Stent Length minus 4 mm |

The mandrel above the stent is advanced towards the axis of the stent on a testing machine having tensile and compressive capabilities and a recordation of force and displacement applied to the stent is recorded. The flexural peak load is the maximum force value in the force-displacement curve. The flexural modulus is the slope of the linear portion of the force-displacement curve. The stents are preconditioned to 37° C. in body temperature water bath for at least one minute prior to 3-point bending testing, and are tested at ambient conditions.

Bend-rotate fatigue life is measured using the following method (the method is based on DIN 50113 (German Institute for Standardization)). Each end of a stent is mounted concentrically on the end of a post and the posts are rotated at the same frequency. The rotational axes of the posts are oriented at an angle of 90° to each other. The distance between the posts is adjusted until the smallest radius along the length of the outer diameter of the stent (worst case bending radius) is 26 mm. The stent is rotated at ≤10 Hz until the stent fractures. The cycles to failure is the number of full rotations made by the stent before the stent breaks. The test environment for bend-rotate fatigue is in air at 37° C.

Stents manufactured according to the techniques and methods disclosed herein have exceptional fatigue resistance as shown in the examples below.

EXAMPLE 1

A 6 mm diameter stent having a structure as shown in FIGS. 5A and 5B was laser cut from binary nitinol alloy tubing SE508 (NDC Corporation, Fremont, Calif.) and expanded and heat treated using the exemplar processes described in conjunction with FIG. 12 (hereinafter referred to as "Stent 6×") to produce material having an upper plateau stress of 355±7.2 MPa and a lower plateau stress of 104±7.2 MPa, an ultimate tensile stress of 1,088±51 MPa, and an elongation of 15.4±2.2%. Stent 6× and competitive 6 mm stents were tested for kink radius, flexural properties, and bend-rotation fatigue endurance. Bend-rotation fatigue endurance subjected the stent struts to a maximum strain of ±3.5%. Percentage strain is defined as change in length divided by original length. Highest strain values are at the stent outer surface, as calculated by finite element analysis using material parameters derived from uncut stent tubing subjected to the same thermomechanical history as stents laser cut from the same tubing. As the table below shows, stent 6× has superior measured characteristics as compared to those of competitive stents.

| Stent | Kink Radius (inches) | Cycles to Failure (#) | Flexural Modulus (g/mm) | Flexural Peak Load (g) |
| --- | --- | --- | --- | --- |
| Competitor B | | 23,315 | 10.03 | 18.18 |
| Competitor CP | 0.375 | | | |
| Competitor CS | | 667,974 | 7.96 | 15.99 |
| Competitor CZ | | | 3.56 | 6.56 |
| Competitor G | | 151,371 | 1.39 | 3.37 |
| Stent P | 0.494 | | 18.46 | 36.16 |
| Stent 6X[1,2] | 0.189 | >20,000,000 | 4.33 | 8.63 |
| | 0.171 | | 3.90 | 8.61 |

[1]Two data sets for kink radius were generated
[2]Two data sets for flexural properties were generated

EXAMPLE 2

A 7 mm diameter stent having a structure substantially similar to that shown in FIGS. 5A and 5B was laser cut from binary nitinol alloy tubing SE508 (NDC Corporation, Fremont, Calif.) and expanded and heat treated using expansion, annealing, and other processes substantially similar to those described in conjunction with FIG. 12 to produce material having an upper plateau stress of 355±7.2 MPa and a lower plateau stress of 104±7.2 MPa, an ultimate tensile stress of 1,088±51 MPa, and an elongation of 15.4±2.2%; it is hereinafter referred to as "Stent 7×". Stent 7× and competitive 7 mm stents were tested for bend-rotation fatigue endurance. As the table below shows, stent 7× has superior measured characteristics as compared to those of a competitive stent.

| Stent | Kink Radius (inches) | Cycles to Failure (#) | Flexural Modulus (g/mm) | Flexural Peak Load (g) |
| --- | --- | --- | --- | --- |
| Competitor B | | 7,800 | | |
| Competitor CS | | 150,000 | | |
| Stent 7X | | >10,000,000 | | |

EXAMPLE 3

An 8 mm diameter stent, having a structure substantially similar to that shown in FIGS. 5A and 5B was laser cut from binary nitinol alloy tubing SE508 (NDC Corporation, Fremont, Calif.) and expanded and heat treated using expansion, annealing, and other processes substantially similar to those described in conjunction with FIG. 12 to produce material having an upper plateau stress of 355±7.2 MPa and a lower plateau stress of 104±7.2 MPa, an ultimate tensile stress of 1,088±51 MPa, and an elongation of 15.4±2.2%. The stent described in the above sentence is hereinafter referred to as "Stent 8×". Along with competitive 8 mm stents, it was tested for kink radius, flexural properties and bend-rotation fatigue endurance. As the table below shows, stent 8× has superior measured characteristics as compared to those of competitive stents.

| Stent | Kink Radius (inches) | Cycles to Failure (#) | Flexural Modulus (g/mm) | Flexural Peak Load (g) |
|---|---|---|---|---|
| Competitor A | 0.400 | | | |
| Competitor B | | 8,758 | | |
| Competitor CP | 0.475 | | | |
| Competitor CS | 0.375 | 12,084 | | |
| Competitor G | | 549,570 | | |
| Stent 8X[1] | 0.195 0.165 | >10,000,000 | 4.46 | 9.10 |

[1] Two data sets for kink radius were generated

In certain embodiments of the invention, the stents of the invention may be designed to resist fracture (as measured by bend-rotate fatigue test) over at least 100,000 cycles, at least 200,000 cycles, at least 500,000 cycles, at least 1,000,000 cycles, at least 2,000,000 cycles, at least 5,000,000 cycles, at least 10,000,000 cycles, or at least 20,000,000 cycles.

An exemplar method of using a stent delivery system to deliver a fatigue resistant stent into a body of a patient is now described. Using techniques well known in the art, a guidewire is percutaneously inserted into a patient's blood vessel and advanced to a region of interest in the patient's body. Using imaging techniques such as fluoroscopy the diseased portion of the vessel is identified and a stent having the correct length and diameter for a treatment site is chosen. With reference to FIGS. 1, 2, 3, 4A, 4B, 5, 5A and 5B self expanding stent delivery system 10, 60 is advanced over the guidewire to the treatment site and by using imaging techniques such as fluoroscopy both ends 12a, 12b of stent 12 are positioned at a correct location relative to the treatment site.

Inner member 14, 64 is held stationary and sheath 16, 66 is withdrawn to expose stent 12. Stent 12 expands into contact with a lumenal wall of the vessel as sheath 16, 66 is withdrawn. Distal interlock 26 prevents stent from compressing axially when sheath 16, 66 is withdrawn, thereby facilitating deployment of distal end 12b of expanded stent at the correct location and reducing forces required to withdraw sheath 16, 66. Mid interlocks 28 (if used) prevent stent from compressing axially when sheath 16, 66 is withdrawn thereby reducing forces required to withdraw sheath 16, 66. Proximal interlocks 27 secure stent to stent delivery catheter until sheath 16, 66 is withdrawn proximally to stent end 12a, thereby thereby reducing forces required to withdraw sheath 16, 66 and facilitating deployment of proximal end 12a of expanded stent at the correct location. After, and optionally, during stent deployment, stent markers 15 are imaged for various reasons including evaluating deployed stent position relative to treatment site, evaluating extent of stent diametrical expansion, and other reasons.

Following implantation of a fatigue resistant stent into a patient the patient may return to the implanting physician for a followup visit. During followup the markers 15 of implanted stent 12, stent 12, or both may be imaged using imaging techniques such as fluoroscopy, ultrasound, or magnetic resonance imaging to assess whether or not stent 12 has fractured, or for other reasons.

While the various embodiments of the present invention have related to stents and stent delivery systems, the scope of the present invention is not so limited. For example, it will be appreciated that the various aspects of the present invention are also applicable to other types of expandable implants and their delivery systems. By way of non-limiting example, other types of expanding implants that can benefit from application of the invention include anastomosis devices, blood filters, grafts, vena cava filters, percutaneous valves, aneurism treatment devices, or other devices.

Modifications and equivalents of the disclosed concepts are intended to be included within the scope of the claims. Further, while choices for materials and configurations may have been described above with respect to certain embodiments, one of ordinary skill in the art will understand that the materials and configurations described are applicable across the embodiments.

What is claimed is:

1. An implant and delivery system comprising an implant comprising a nickel titanium alloy tube having a first end and a second end, said tube having an Austenite finish temperature suitable for use in a patient, said tube is shape set to a first substantially longitudinal configuration, and said tube having a kink radius of less than 0.195 inches; and a catheter for delivering the implant to a delivery site, the catheter constraining the implant until release of the implant from the catheter at which occurrence, the implant self expands to an enlarged condition thereof.

2. A surgical system comprising:
a catheter; and
an implant disposed within the catheter in a collapsed condition to be delivered by the catheter to a delivery site and being releasable from the catheter to expand to an enlarged condition, the implant comprising a nickel titanium alloy tube having a first end and a second end, said tube having an Austenite finish temperature suitable for use as a stent in a patient, said tube is shape set to a first substantially longitudinal configuration, and said tube having a kink radius of no greater than 0.195 inches, the implant being shape set by a process comprising:
  (a) restraining the implant on a mandrel having a first diameter and annealing the implant within a first temperature range selected to dissolve nickel rich precipitates in the implant:
  (b) after (a), with the implant remaining on the mandrel, annealing the implant within a second temperature range that is lower than the first temperature range; and selected to set the Austenite finish temperature of the implant.

3. The surgical system of claim 2, wherein the second temperature range is 482-488° C.

4. The surgical system of claim 2, wherein the first temperature range is 598-602° C.

5. The surgical system of claim 2, wherein the tube has an ultimate tensile strength of between 1.032 MPa and 1134 MPa.

6. The surgical system of claim 2, wherein, prior to (a), restraining the implant on a mandrel of a second diameter and annealing the implant within a third temperature range, the second diameter being less than the first diameter and the third temperature range being less than the first temperature range.

7. An implant and delivery system, comprising:
a stent implant comprising a nickel titanium alloy tube having a first end and a second end, said tube having an Austenite finish temperature suitable for use in a patient, said tube is shape set to a first substantially longitudinal configuration, and said tube having a kink radius of less than 0.195 inches, the implant being dimensioned and adapted to transition from a constrained condition to an expanded condition, the implant being shape set by a process comprising:

(a) restraining the implant on a mandrel having a first diameter and annealing the implant within a first temperature range selected to dissolve nickel rich precipitates in the implant;
(b) after (a), with the implant remaining on the mandrel, annealing the implant within a second temperature range lower than the first temperature range and selected to set the Austenite finish temperature; and a catheter for delivering the implant to a delivery site, the catheter dimensioned to maintain the implant in the constrained condition, whereby upon release of the implant from the catheter, the implant moves to the expanded condition thereof.

8. The implant and delivery system of claim 7, wherein the second temperature range is 482-488° C.

9. The implant and delivery system of claim 7, wherein the first temperature range is 598-602° C.

10. The implant and delivery system of claim 7, wherein the implant has an ultimate tensile strength of between 1.032 MPa and 1134 MPa.

11. The implant and delivery system of claim 7, wherein the implant has a fatigue life of at least 10,000,000 cycles.

12. The implant and delivery system of claim 7, wherein the implant has a fatigue life of at least 20,000,000 cycles.

13. The implant and delivery system of claim 7, wherein the tube comprises 50-52 atomic percent nickel.

14. The implant and delivery system of claim 7, wherein (a) comprises annealing the implant at 598-602° C. for 45 to 60 seconds.

15. The implant and delivery system of claim 7, wherein (b) comprises annealing the implant at 482-488° C. for 5 minutes.

16. The implant and delivery system of claim 7, wherein the tube comprises 50-52 atomic weight percent nickel and the balance comprises titanium and small amounts of impurities.

17. The implant and delivery system of claim 7, wherein, prior to (a), restraining the implant on a mandrel of a second diameter and annealing the implant within a third temperature range, the second diameter being less than the first diameter and the third temperature range being less than the first temperature range.

18. An implant and delivery system, comprising:
an implant member suitable for use as a stent in a patient, said implant member including a nickel titanium alloy tube having a first end and a second end, said tube having an Austenite finish temperature suitable for use as a stent in a patient, and having a kink radius of less than 0.195 inches;
wherein said tube is shape set to a first substantially longitudinal configuration, and
wherein said tube has an ultimate tensile strength between 1.032 MPa and 1134 MPa; and
a catheter for delivering the implant memter member to a delivery site, wherein the implant is retained on the catheter in a collapsed state, wherein the implant memter is selectively releasable from the catheter, wherein when the implant member is released from the catheter, the implant member is expandable to an enlarged state to abut an inner wall of a body lumen.

19. The implant and delivery system of claim 18, wherein the kink radius of the implant memter is no greater than 0.189 inches.

20. The implant and delivery system of claim 18, wherein the kink radius of the implant member is no greater than 0.171 inches.

21. The implant and delivery system of claim 18, wherein the kink radius of the implant member is no greater than 0.165 inches.

* * * * *

UNITED STATES PATENT AND TRADEMARK OFFICE
CERTIFICATE OF CORRECTION

PATENT NO. : 8,562,668 B2  
APPLICATION NO. : 11/764336  
DATED : October 22, 2013  
INVENTOR(S) : Ma et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 648 days.

Signed and Sealed this  
Seventh Day of April, 2015

Michelle K. Lee  
*Director of the United States Patent and Trademark Office*